United States Patent [19]

Inomata et al.

[11] Patent Number: 5,861,528
[45] Date of Patent: Jan. 19, 1999

[54] PROCESS FOR PREPARING DIELS-ALDER ADDITION PRODUCT FROM CONJUGATED DIOLEFIN AND ACRYLONITRILE

[75] Inventors: Masamitsu Inomata, Takaishi; Masahiro Takeno, Mobara; Akio Numa, Mobara; Hiroki Mizutani, Mobara; Masanobu Ebina, Yokohama; Isao Fukada, Mobara, all of Japan

[73] Assignee: Mitsui Chemicals, Inc., Tokyo, Japan

[21] Appl. No.: 785,827

[22] Filed: Jan. 15, 1997

[30] Foreign Application Priority Data

Jan. 22, 1996 [JP] Japan ................................ 8-008017
Jan. 22, 1996 [JP] Japan ................................ 8-008018

[51] Int. Cl.$^6$ .................................................. C07C 255/00
[52] U.S. Cl. ........................... 558/365; 558/366; 558/377
[58] Field of Search .................................... 558/365, 366, 558/377

[56] References Cited

U.S. PATENT DOCUMENTS 3,359,285  12/1967  Landis et al. ............................ 558/365

FOREIGN PATENT DOCUMENTS

| | | |
|---|---|---|
| 1518552 | 7/1969 | Germany . |
| 2432630 | 1/1976 | Germany . |
| 51-34139 | 3/1976 | Japan . |
| 54-9198 | 4/1979 | Japan . |
| 57-7131 | 2/1982 | Japan . |
| 59-51533 | 12/1984 | Japan . |
| 61-165338 | 7/1986 | Japan . |
| 62-167733 | 7/1987 | Japan . |
| 7-188147 | 7/1995 | Japan . |
| 0659567 | 4/1979 | U.S.S.R. ................................ 558/365 |

*Primary Examiner*—Peter O'Sullivan
*Attorney, Agent, or Firm*—Burns, Doane, Swecker & Mathis, L.L.P.

[57] ABSTRACT

In a process for preparing a Diels-Alder addition product of a conjugated diolefin and acrylonitrile by reacting the conjugated diolefin with acrylonitrile, a vessel type reactor is used. The pressure of the gaseous phase in the reactor is increased by using an inert gas in the reaction. A premixed solution of the conjugated diolefin or a compound which produces the conjugated diolefin in the reactor and acrylonitrile is released through an upper portion of the reactor into the gaseous phase and then dropped into a liquid phase to react. A reaction product is taken out through a lower portion of the reactor. The process can be carried out continuously in a safe manner over an extended period of time without any adhesion of an insoluble polymer to the reactor or to the inlet or outlet pipes, and without sudden pressure fluctuations.

13 Claims, 4 Drawing Sheets

Sheet 1

PROCESS FOR PREPARING DIELS-ALDER ADDITION PRODUCT FROM CONJUGATED DIOLEFIN AND ACRYLONITRILE

BACKGROUND OF THE INVENTION (1) Field of the Invention

The present invention relates to a process for preparing a Diels-Alder addition product of a conjugated diolefin and acrylonitrile by reacting the conjugated diolefin with acrylonitrile.

(2) Description of the Related Art

It is known to prepare a Diels-Alder addition product of a conjugated diolefin and acrylonitrile by reacting the conjugated diolefin with acrylonitrile. This is a thermal reaction and thus is desirably conducted at elevated temperatures. However, when the reaction is carried out at a high temperature, an increased amount of polymers are formed in the reaction solution.

These polymers can be insoluble in the reaction solution and can adhere to or deposit on inner surfaces at or around an inlet of feed and an outlet of the reaction solution. This interferes with the operation of the reaction. Thus, processes have been proposed which add various polymerization inhibitors to the reaction solution to inhibit the by-production of these polymers and to thereby avoid the above-mentioned problems. In order to avoid polymerization of the diolefin or olefin used in a Diels-Alder reaction, the following processes are known: Japanese Patent Publication No. 54-9198 discloses the use of an N-nitrosoamine compound; Japanese Patent Laid-Open No. 61-165338 discloses the use of an alkylphenol compound; Japanese Patent Publication No. 57-7131 discloses the use of a p-phenylenediamine compound; and Japanese Patent Laid-Open No. 62-167733 discloses the use of a hydroxylamine compound.

Alternatively, in a process for preparing cyanonorbornene through a Diels-Alder reaction between acrylonitrile and a conjugated diolefin that is produced from dicyclopentadiene, Japanese Patent Laid-Open No. 7-188147 discloses performing the reaction in the presence of an N-nitrosoamine compound, and Japanese Patent Publication No. 59-51533 discloses adding cyanonorbornene before adding raw material of the reaction.

Japanese Patent Laid-Open No. 51-34139 proposes a process for keeping the raw material in a liquid phase by feeding the raw material into the reaction solution through a lower portion of the reactor and taking out the reaction solution through an upper portion of the reactor to achieve reaction under a pressure higher than a pressure generated spontaneously during the reaction at a given temperature, as a way of improving the yield of cyanonorbornene while reducing the amount of by-produced polymers in a reaction between dicyclopentadiene and acrylonitrile.

Studies made by the present inventors have revealed that the reaction between a conjugated diolefin and acrylonitrile may tend to produce a highly insoluble polymer in the reactor or in the inlet or outlet pipe of the reactor, or may sometimes be accompanied by danger, depending on the methods and aspects used.

More specifically, the present inventors have carried out various reactions using both a so-called tubular reactor in which the conjugated diolefin and acrylonitrile are heated and reacted in a spiral pipe, and a vessel type reactor. In the so-called tubular reactor, it was found that insoluble polymers adhere to the inner surface of the pipe which may then clog the pipe. Thus, this process is hardly applicable to continuous production.

On the other hand, the vessel type reactor does not suffer from adhesion of the insoluble polymers to the inner surface thereof when the reaction is carried out with the reactor completely filled with a solution. However, the present inventors have found that this process is quite dangerous because of sudden change in pressure in the reactor. The present inventors have also found that this process can produce insoluble polymers which adhere to pipes through which the raw material is supplied to the reaction solution or to a discharge portion of the pipes and create a possibility of clogging the pipes. The process described in the above-mentioned Japanese Patent Laid-Open No. 51-34139 is thus revealed to be effective as a process for improving the yield of cyanonorbornene while reducing the by-produced amount of the polymers, but such process is far from being a safe.

As described above, there are some conventional processes that are directed to inhibiting the production of insoluble polymers in the reaction solution during the reaction. However, there is no description of a reactor that can effectively inhibit production of the insoluble polymers. Nor is there a description of a process for carrying out the reaction in a safe manner.

SUMMARY OF THE INVENTION

Accordingly, it is an object of the present invention to provide a process for preparing a Diels-Alder addition product of a conjugated diolefin and acrylonitrile that is industrially applicable and that can be carried out in a safe manner and can effectively inhibit production of insoluble polymers.

More specifically, the present invention provides a process for preparing an addition product of a conjugated diolefin and acrylonitrile, which comprises the steps of: providing a vessel type reactor; increasing the pressure of the gaseous phase in the reactor by introducing an inert gas therein; releasing a premixed solution of the conjugated diolefin or a compound which produces the conjugated diolefin in the reactor and acrylonitrile through an upper portion of the reactor into the gaseous phase and dropping the mixed solution into the liquid phase in the reactor; and taking out a reaction product through a lower portion of the reactor. This process allows for the reaction to be carried out in a safe manner continuously over an extended period of time.

Figure 1:
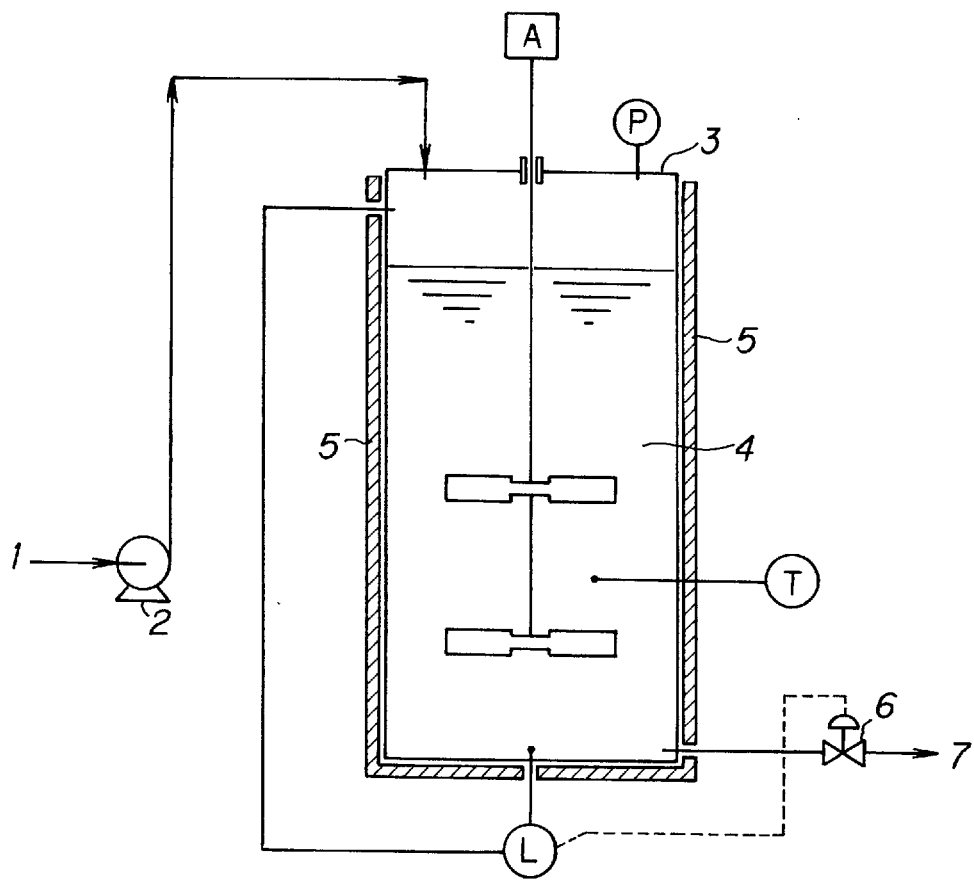
FIG. 1 shows the reactor used in Examples 1 through 12, 14 and 15, and Comparative Examples 1, 2 and 7.

The reference numerals and symbols shown in the figures represent the following:

1: a raw material solution;
2: a metering pump;
3: a reactor;
4: a reaction solution;

5: an electric heater;

6: an automatic control valve;

7: a solution of a Diels-Alder addition product from a conjugated diolefin and acrylonitrile;

8: an equalizing pipe;

9: a gas-liquid separator;

10: a heat medium;

A: a stirrer;

P: pressure gauge;

T: a thermometer; and

L: a differential pressure type level gauge.

DETAILED DESCRIPTION OF THE PREFERRED EMBODIMENTS

In the present invention, any vessel type reactor may used for carrying out the reaction between the conjugated diolefin and acrylonitrile so long as the vessel is capable of holding liquid therein and can be sealed. However, the typical reactor is cylindrical, spherical or reverse conical, or a combination thereof.

In the present invention, the reaction between the conjugated diolefin and acrylonitrile is carried out in the liquid phase. A gaseous phase is provided in the reactor. The gaseous phase can be pressurized by using an inert gas. In this event, an excessively small volume of the gaseous phase is accompanied by considerable danger because the pressure in the reactor tends to change or fluctuate suddenly. On the other hand, an excessively large volume of the gaseous phase may be disadvantageous when considering the volume efficiency. It is thus preferable to carry out the reaction with a gaseous phase volume in the range of 10–50% relative to the entire volume of the reactor. It is more preferable that the reaction is carried out with a gaseous phase volume in the range of 20–40% relative to the entire volume of the reactor.

The pressure during the reaction in the present invention is preferably within the range of 6–70 $kg/cm^2$ .G, depending on the kind of conjugated diolefin or the kind of compound from which the conjugated diolefin is produced in the reactor used. The inert gas used for increasing the pressure may be any gas so long as it has no reactivity with the raw material or the reaction product and does not significantly absorb them. More specifically, the gas used may be at least one selected from the group consisting of nitrogen, argon, helium, methane, ethane, propane, n-butane, and isobutane. Of these, nitrogen can typically be used advantageously because it is readily available. A satisfactory effect can be obtained with nitrogen.

For example, the pressure during the reaction is preferably within the range of 6–30 $kg/cm^2$.G, and more preferably within the range of 6–10 $kg/cm^2$.G when the compound from which the conjugated diolefin is produced is dicyclopentadiene.

It is also preferable that the reaction is carried out at a pressure ranging from 50 to 70 $kg/cm^2$.G and that the inert gas used for increasing the pressure is at least one selected from the group consisting of nitrogen, argon, helium, methane and ethane, when the conjugated diolefin is butadiene.

Furthermore, it is preferable that the reaction is carried out at a pressure ranging from 30 to 50 $kg/cm^2$.G and that the inert gas used for increasing the pressure is at least one selected from the group consisting of nitrogen, argon, helium, methane, ethane and propane, when the conjugated diolefin is isoprene.

In the present invention, the conjugated diolefin or the compound from which the conjugated diolefin is produced in the reactor and acrylonitrile, which are the raw materials, are mixed in advance. The resultant mixed solution is continuously introduced into an upper portion of the reactor into the gaseous phase. The mixed solution then drops into the liquid phase to achieve the reaction. This is a significantly important factor for continuously preparing addition products of the conjugated diolefin and acrylonitrile in a stable manner over an extended period of time without producing polymers in a pipe through which the raw material is supplied. The reaction product is subsequently taken out through a lower portion of the reactor.

If the conjugated diolefin or the compound from which the conjugated diolefin is produced in the reactor and acrylonitrile are fed to the reactor separately rather than together as a mixture, an insoluble polymer tends to form and adhere to surfaces at or around the reactor inlet for the raw materials, especially the inlet for acrylonitrile. Similarly, if a mixed solution of the conjugated diolefin or the compound from which the conjugated diolefin is produced in the reactor and acrylonitrile are fed directly into the reaction solution, a large amount of insoluble polymers will also tend to form and adhere to the inlet pipe. In either case, the pipe is likely to be clogged with the insoluble polymers. Therefore, it is very difficult to continuously prepare the addition products of the conjugated diolefin and acrylonitrile in a stable manner over an extended period of time.

In the present invention, the reaction between the conjugated diolefin or the compound from which the conjugated diolefin is produced in the reactor and acrylonitrile is typically carried out in the presence of a compound that inhibits production of polymers. The compound used may be any one of the various compounds typically used for Diels-Alder reactions. Of these, it is particularly preferable in the present invention to use an N-nitrosoamine compound or a p-phenylenediamine compound. These compounds are capable of very effectively inhibiting production of a soluble polymer which is a precursor of the insoluble polymer that is otherwise produced during the reaction between the conjugated diolefin or the compound from which the conjugated diolefin is produced in the reactor and acrylonitrile.

Preferable examples of the N-nitrosoamine compound include N-nitrosodimethylamine, N-nitrosodiethylamine, N-nitrosomethylethylamine, N-nitrosodiphenylamine, N-nitrosobenzylaniline and 4-nitroso-N,N-dimethylaniline. Preferable examples of the p-phenylenediamine compound include N-phenyl-N'-isopropyl-p-phenylenediamine. These compounds may be used alone or as a mixture of two or more thereof.

The amount of the compound that inhibits the production of polymers is typically within the range of 0.003–1% by weight, and preferably within the range of 0.005–0.3% by weight relative to the total amount of the conjugated diolefin or the compound from which the conjugated diolefin is produced in the reactor and acrylonitrile. The compound that inhibits the production of polymers is merely required to be present in the reaction solution during the reaction. For example, the compound may be added in advance of the conjugated diolefin or the compound from which the conjugated diolefin is produced in the reactor. Alternatively, the compound may be added to the mixture of the conjugated diolefin or the compound from which the conjugated diolefin is produced in the reactor and acrylonitrile.

In the present invention, the temperature for carrying out the reaction between the conjugated diolefin or the compound from which the conjugated diolefin is produced in the reactor and acrylonitrile is 180°–200° C., more preferably 185°–200° C., and most preferably 190–200° C. A reaction temperature below 180° C. tends to reduce the yield of the resultant addition product and leave a large amount of unreacted materials in the reaction solution, although the production of the soluble polymer can be inhibited. On the other hand, a reaction temperature greater than 200° C. tends to cause significant production of the soluble polymers in the reaction solution. Accordingly, it is preferable that the reaction is carried out in the above-mentioned temperature ranges.

In the present invention, the reaction between the conjugated diolefin and acrylonitrile is, in theory, a reaction between 1 mole of conjugated diolefin and 1 mole of acrylonitrile. However, it is preferable that the reaction be carried out using 1–1.5 moles of acrylonitrile per 1 mole of conjugated diolefin. An amount of acrylonitrile less than 1 mole tends to increase the production of by-products while an amount larger than 1.5 moles tends to cause a large amount of unreacted acrylonitrile to remain. In addition, amounts of less than 1 and greater than 1.5 are not preferable because the purification operation that may be required to separate out the undesired reaction components may be complicated. Accordingly, it is preferable that the reaction is carried out by using, for example, 2–3 moles of acrylonitrile per 1 mole of dicyclopentadiene when the latter is used as the compound from which the conjugated diolefin is produced in the reactor.

Although it depends on the reaction temperature, the reaction time may typically be within the range of 0.1–6 hours when considering to obtain a high yield of the addition product and high production thereof. The reaction time may be shorter or longer than the one described above, if necessary.

To implement the process according to the present invention, the reaction is typically carried out continuously by continuously feeding a mixed solution of the conjugated diolefin or the compound from which the conjugated diolefin is produced in the reactor and acrylonitrile, which are the raw materials, into the reactor by using, for example, a metering pump, and supplying the inert gas to the reaction to adjust the pressure. However, it is also effective in a batch process to carry out the reaction at a higher pressure which can be applied by introducing the inert gas to the reaction. For a continuous process, the conjugated diolefin or the compound from which the conjugated diolefin is produced in the reactor and acrylonitrile are mixed in advance and supplied to the reactor together rather than being supplied thereto separately.

EXAMPLES

The advantages of the present invention are described below in conjunction with a set of examples and comparative examples.

Example 1

The reactor used was a pressure autoclave made of stainless steel and equipped with a stirrer having an inner volume of 1,500 ml, the essentials of which are shown in FIG. 1. Before initiating the reaction, 1,015 ml of cyanonorbornene were placed in the autoclave. The content of the reactor was heated to 170° C. while stirring at a rotating speed of 600 rpm. Next, dicyclopentadiene and acrylonitrile were mixed in a molar ratio of 1:2.5. N-nitrosodiphenylamine was added to the mixed solution such that the content thereof is 0.1% by weight to provide a raw material solution. The raw material solution was continuously supplied to the autoclave by a metering pump such that the residence time becomes 4 hours. During the reaction, the liquid level in the reactor was kept such that the volume of the gaseous phase over the reaction solution in the reactor is 30% relative to the entire volume of the reactor. In addition, nitrogen gas was fed to the reactor to adjust the pressure in the autoclave to 8 $kg/cm^2$.G. Furthermore, the temperature of the liquid was kept at 190° C. for the continuous reaction.

As a result, cyanonorbornene was continuously obtained with an average yield of 93% by mole based on cyclopentadiene obtained by decomposition of dicyclopentadiene used as the raw material. In addition, the amount of the soluble polymer produced in the reaction solution immediately after the initiation of the reaction was 0.002% by weight, which did not change significantly in 60 days after the initiation of the operation. In addition, the operation was stopped after 70 days from the initiation to inspect in detail the inlet for the raw material, the inner wall, the outlet for the reaction solution and the stirrer of the autoclave. No insoluble polymer was found to adhere to those surfaces.

Gas chromatography was used for the analysis of the reaction solution. The amount of the soluble polymer produced was determined by diluting the reaction solution with tetrahydrofuran and subjecting the resultant solution to gel permeation chromatography.

Example 2

Example 1 was repeated except that the liquid temperature during the reaction was kept at 200° C. As a result, cyanonorbornene was continuously obtained with an average yield of 96% by mole. In this example, the amount of the soluble polymer produced was 0.003% by weight at the beginning of the reaction, which did not change significantly in 60 days after the initiation of the reaction. In addition, the operation was stopped after 80 days from the initiation to inspect in detail the inlet for the raw material, the inner wall, the outlet for the reaction solution and the stirrer of the autoclave. No insoluble polymer was found to adhere to those surfaces.

Example 3

Example 1 was repeated except that N-nitrosodiethylamine was used in place of N-nitrosodiphenylamine. N-nitrosodiethylamine was added to a mixed solution of dicyclopentadiene and acrylonitrile in an amount of 0.005% by weight. As a result, cyanonorbornene was continuously obtained with an average yield of 93% by mole. In this example, the amount of the soluble polymer produced was 0.01% by weight at the beginning of the reaction, which did not change significantly in 60 days after the initiation of the reaction. In addition, the operation was stopped after 80 days from the initiation to inspect in detail the inlet for the raw material, the inner wall, the outlet for the reaction solution and the-stirrer of the autoclave. No insoluble polymer was found to adhere to those surfaces.

Example 4

Example 1 was repeated except that the liquid temperature during the reaction was kept at 180° C. As a result, cyanonorbornene was continuously obtained with an average yield of 87% by mole. In this example, the amount of the soluble polymer produced was 0.001% by weight at the beginning of the reaction, which did not change significantly in 20 days after the initiation of the reaction.

Example 5

Example 1 was repeated except that N-phenyl-N'-isopropyl-p-phenylenediamine was used in place of N-nitrosodiphenylamine in the same amount. As a result, cyanonorbornene was continuously obtained with an average yield of 93% by mole. In this example, the amount of the soluble polymer produced was 0.15% by weight at the beginning of the reaction, which did not change significantly in 60 days after the initiation of the reaction. In addition, the operation was stopped after 70 days from the initiation to inspect in detail the inlet for the raw material, the inner wall, the outlet for the reaction solution and the stirrer of the autoclave. No insoluble polymer was found to adhere to those surfaces.

Example 6

Example 1 was repeated except that 4-nitroso-N,N-dimethylaniline was used in place of N-nitrosodiphenylamine in the same amount and that the nitrogen gas was supplied to adjust the pressure in the autoclave to 7 $kg/cm^2$.G. As a result, cyanonorbornene was continuously obtained with an average yield of 93% by mole. In this example, the amount of the soluble polymer produced was 0.13% by weight at the beginning of the reaction, which did not change significantly in 60 days after the initiation of the reaction. In addition, the operation was stopped after 70 days from the initiation to inspect in detail the inlet for the raw material, the inner wall, the outlet for the reaction solution and the stirrer of the autoclave. No insoluble polymer was found to adhere to those surfaces.

Example 7

Example 1 was repeated except that the raw material solution was supplied in a manner that the residence time was 1 hour. As a result, cyanonorbornene was continuously obtained with an average yield of 90% by mole. In this example, the amount of the soluble polymer produced was 0.001% by weight at the beginning of the reaction, which did not change significantly in 60 days after the initiation of the reaction. In addition, the operation was stopped after 70 days from the initiation to inspect in detail the inlet for the raw material, the inner wall, the outlet for the reaction solution and the stirrer of the autoclave. No insoluble polymer was found to adhere to those surfaces.

Example 8

Example 1 was repeated except that the volume of the gaseous phase over the reaction solution in the reactor was kept at 20% relative to the entire volume of the reactor. As a result, cyanonorbornene was continuously obtained with an average yield of 93% by mole. In this example, the amount of the soluble polymer produced was 0.002% by weight at the beginning of the reaction, which did not change significantly in 60 days after the initiation of the reaction. In addition, the operation was stopped after 70 days from the initiation to inspect in detail the inlet for the raw material, the inner wall, the outlet for the reaction solution and the stirrer of the autoclave. No insoluble polymer was found to adhere to those surfaces.

Example 9

Example 1 was repeated except an argon gas was used in place of the nitrogen gas to adjust the pressure. As a result, cyanonorbornene was continuously obtained with an average yield of 93% by mole. In this example, the amount of the soluble polymer produced was 0.002% by weight at the beginning of the reaction, which did not change significantly in 60 days after the initiation of the reaction. In addition, the operation was stopped after 70 days from the initiation to inspect in detail the inlet for the raw material, the inner wall, the outlet for the reaction solution and the stirrer of the autoclave. No insoluble polymer was found to adhere to those surfaces.

Example 10

Example 1 was repeated except that a methane gas was used in place of the nitrogen gas to adjust the pressure. As a result, cyanonorbornene was continuously obtained with an average yield of 92% by mole. In this example, the amount of the soluble polymer produced was 0.003% by weight at the beginning of the reaction, which did not change significantly in 60 days after the initiation of the reaction. In addition, the operation was stopped after 70 days from the initiation to, inspect in detail the inlet for the raw material, the inner wall, the outlet for the reaction solution and the stirrer of the autoclave. No insoluble polymer was found to adhere to those surfaces.

Example 11

Example 1 was repeated except that a propane gas was used in place of the nitrogen gas to adjust the pressure. As a result, cyanonorbornene was continuously obtained with an average yield of 91% by mole. In this example, the amount of the soluble polymer produced was 0.003% by weight at the beginning of the reaction, which did not change significantly in 60 days after the initiation of the reaction. In addition, the operation was stopped after 70 days from the initiation to inspect in detail the inlet for the raw material, the inner wall, the outlet for the reaction solution and the stirrer of the autoclave. No insoluble polymer was found to adhere to those surfaces.

Example 12

Example 1 was repeated except that an n-butane gas was used in place of the nitrogen gas to adjust the pressure. As a result, cyanonorbornene was continuously obtained with an average yield of 90% by mole. In this example, the amount of the soluble polymer produced was 0.005% by weight at the beginning of the reaction, which did not change significantly in 40 days after the initiation of the reaction. In addition, the operation was stopped after 50 days from the initiation to inspect in detail the inlet for the raw material, the inner wall, the outlet for the reaction solution and the stirrer of the autoclave. No insoluble polymer was found to adhere to those surfaces.

Comparative Example 1

Example 1 was repeated except that the reaction was conducted under a pressure of 4–5 $kg/cm^2$.G, which was generated spontaneously in the reactor without supplying the nitrogen gas. As a result, the amount of the soluble polymer produced was 0.003% by weight at the beginning of the reaction. The operation was stopped after 30 days from the initiation to inspect in detail the inside the autoclave. Insoluble polymers were found to have adhered to the inlet for the raw material and the inner wall of the autoclave.

Comparative Example 2

Example 1 was repeated except that the liquid temperature during the reaction was kept at 210° C. and the reaction was conducted under a pressure of 9 $kg/cm^2$.G adjusted with nitrogen gas. As a result, the amount of the soluble polymer produced was 0.01% by weight at the beginning of the reaction, which increased to 1% in 5 days after the initiation of the operation. The operation was stopped after 10 days from the initiation because it became difficult to supply the raw material. An inspection of the inside of the autoclave revealed that a significant amount of insoluble polymers had adhered to the inlet for the raw material and the inner wall of the autoclave.

Comparative Example 3

Figure 2:
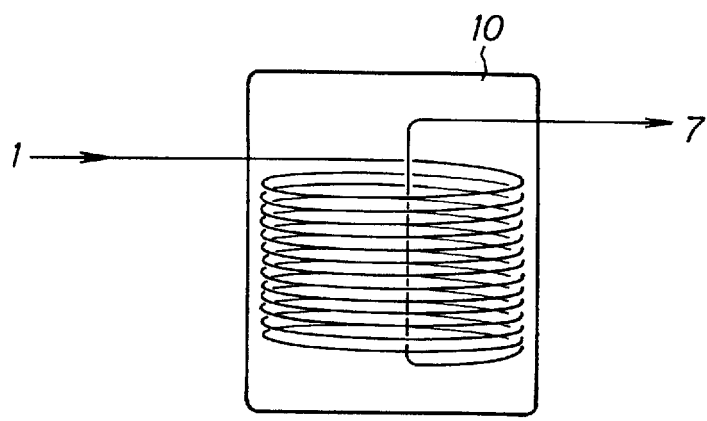
FIG. 2 shows the reactor used in Comparative Example 3.

The reactor used was a stainless pipe having an inner diameter of 3 mm and a length of 4 m. The pipe was formed into a spiral having a number of coils. The essentials of the reactor are shown in FIG. 2. The same raw material solution as prepared in Example 1 was passed through the pipe. The temperature of the oil outside thereof, which served as the heat medium, was increased to 190° C. and the reaction was carried out continuously with a residence time of 4 hours.

In this comparative example, it became difficult to supply the raw material 1 day after initiation of the reaction. As a result, the operation was stopped at that time. The inside of the tube/reactor was inspect ed to find that a large amount of insoluble polymers had adhered thereto and that the pipe was clogged.

Comparative Example 4

Figure 3:
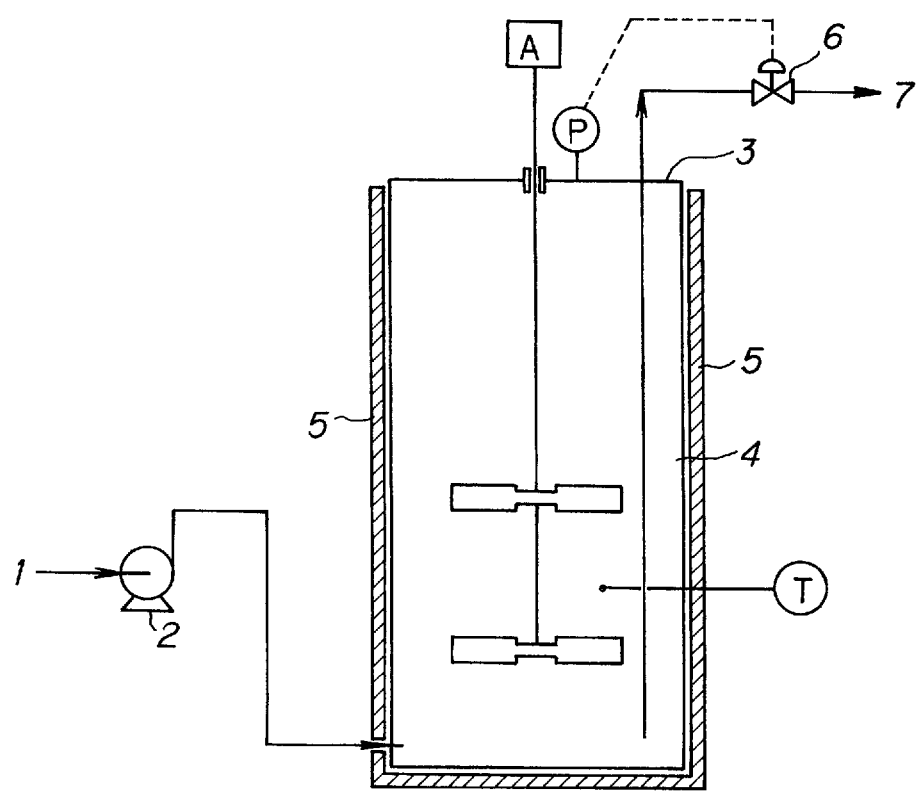
FIG. 3 shows the reactor used in Comparative Examples 4 and 9.

Example 1 was repeated except that the reactor shown in FIG. 3 was used. The reactor was completely filled with the reaction solution to prepare cyanonorbornene. However, this example suffered from a considerable fluctuation in pressure in the reactor and an increase in the inner temperature.

The pressure suddenly fluctuated in the range of 5–30 $kg/cm^2$.G. There was a great possibility of damaging the reactor and auxiliary facilities. It was thus found that it was difficult to prepare cyanonorbornene continuously in a safe manner.

Comparative Example 5

Figure 4:
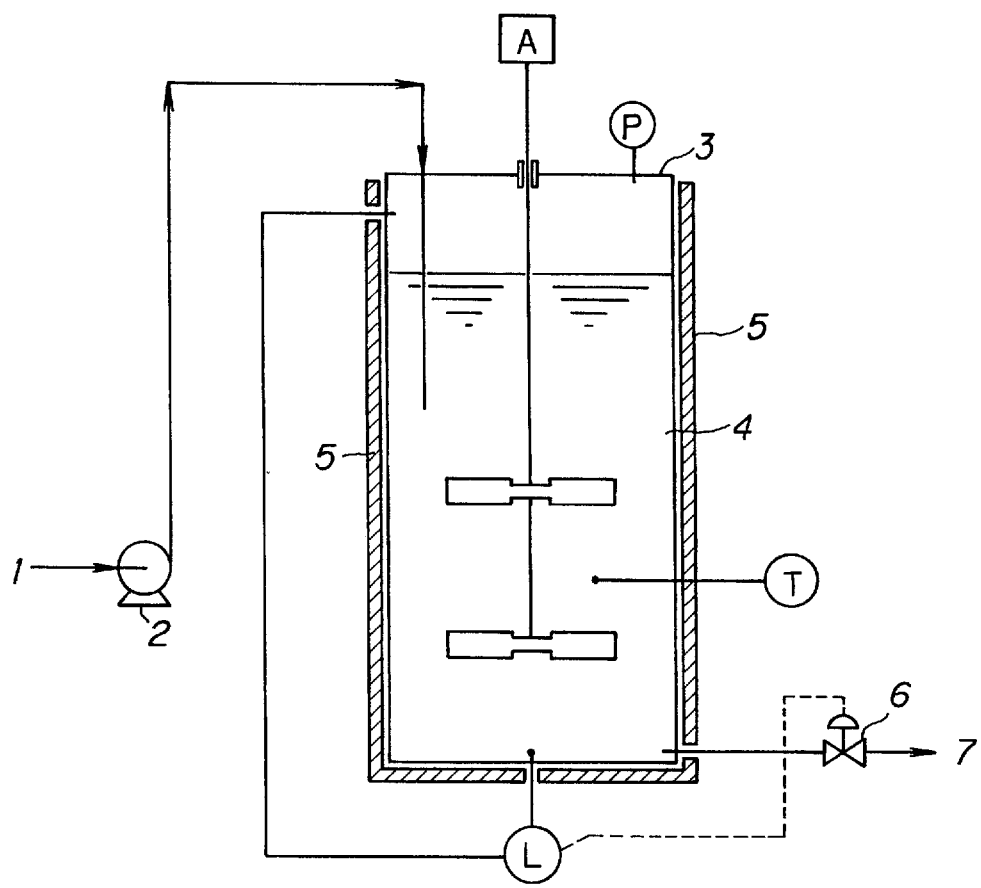
FIG. 4 shows the reactor used in Comparative Examples 5 and 8.

Example 1 was repeated to try to continuously prepare cyanonorbornene except that the pipe for supplying the raw material was positioned directly in the liquid in the vessel type reactor, as shown in FIG. 4. It became difficult to supply the raw material 3 days after initiation of the reaction, so the operation was stopped. The inside of the reactor was inspected to find that a large amount of insoluble polymers had adhered to the inner wall of the supply pipe, especially at or around the surface of the outlet pipe for the raw material. The pipe was clogged.

Comparative Example 6

Figure 5:
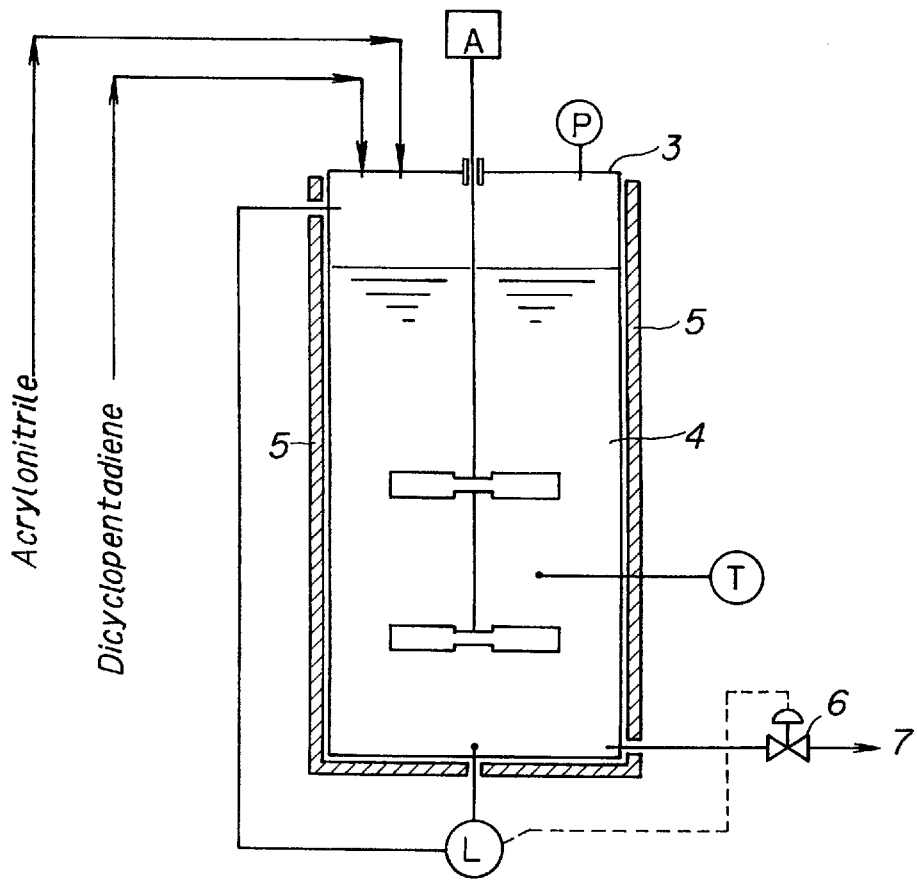
FIG. 5 shows the reactor used in Comparative Example 6.

Example 1 was repeated to try to continuously prepare cyanonorbornene except that acrylonitrile and dicyclopentadiene, which were the raw materials, were independently supplied to the gaseous phase in the reactor without being mixed with each other in advance, as shown in FIG. 5. It became difficult to supply acrylonitrile 2 days after initiation of the reaction, so the operation was stopped. The inside of the reactor was inspected to find that a large amount of insoluble polymers had adhered to the inner wall of the pipe for feeding acrylonitrile, especially at or around the surface of the outlet pipe for acrylonitrile.

Comparative Example 7

Example 1 was repeated except that hydroquinone was used in place of N-nitrosodiphenylamine in the same amount. As a result, cyanonorbornene was continuously obtained with an average yield of 83% by mole. However, it became difficult to supply the raw material 4 days after initiation of the reaction, so the operation was stopped. The inside of the reactor was inspected to find that a large amount of insoluble polymers had adhered to the inner wall of the pipe for feeding the raw material, especially at or around the surface of the outlet pipe for the raw material. The pipe was clogged.

Example 13

Figure 6:
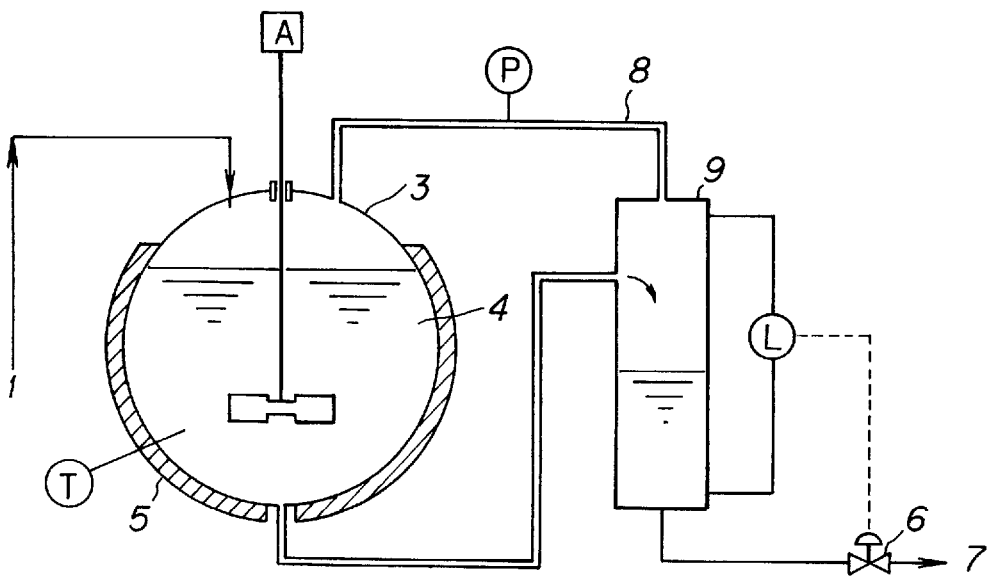
FIG. 6 shows the reactor used in Example 13.

Example 1 was repeated except that the reactor used was a spherical type reactor; the essentials of which are shown in FIG. 6. The volume of the gaseous phase was 30% relative to the entire volume of the reactor. The reaction solution was flowed out to a gas-liquid separator to keep the liquid in the reactor level. Also in this example, the pressure in the reactor could be kept at 8 $kg/cm^2$.G. The supplying amount of the raw material was not changed or fluctuated. Cyanonorbornene was obtained continuously with an average yield of 93% by mole. The operation was stopped 50 days after initiation of the reaction to inspect in detail the inside of the reactor, the inlet pipe for the raw material and the outlet pipe for the reaction solution. No insoluble polymer was found to adhere to those surfaces.

Example 14

The reactor used was a pressure autoclave made of stainless steel and equipped with a stirrer having an inner volume of 1,500 ml, the essentials of which are shown in FIG. 1. Before initiating the reaction, 1,015 ml of cyanocyclohexene were placed in the autoclave. The content of the reactor was heated to 150° C. while stirring at a rotating speed of 600 rpm. Next, 1,3-butadiene and acrylonitrile were mixed in a pressurized vessel in a molar ratio of 1:1.2. N-nitrosodiphenylamine was added to the mixed solution such that the content thereof is 0.1% by weight to provide a raw material solution. The raw material solution was continuously supplied to the autoclave by a metering pump such that the residence time becomes 1 hour. During the reaction, the liquid level in the reactor was kept such that the volume of the gaseous phase over the reaction solution in the reactor is 30% relative to the entire volume of the reactor. In addition, nitrogen gas was fed to the reactor to adjust the pressure in the autoclave to 65 $kg/cm^2$.G. Furthermore, the temperature of the liquid was kept at 185° C. for the continuous reaction.

As a result, cyanocyclohexene was continuously obtained with an average yield of 83% by mole based on 1,3-butadiene used as the raw material. The pressure in the reactor was not changed or fluctuated suddenly in this example. Furthermore, the supplying amount of the raw material was not changed. The operation was stopped 15 days after initiation of the reaction to inspect in detail the inside of the reactor, the inlet pipe for the raw material and the outlet pipe for the reaction solution. No insoluble polymer was found to adhere to those surfaces.

Example 15

The reactor used was a pressure autoclave made of stainless steel and equipped with a stirrer having an inner volume of 1,500 ml, the essentials of which are shown in FIG. 1. Before initiating the reaction, 1,015 ml of methylcyanocyclohexene were placed in the autoclave. The content of the reactor was heated to 150° C. while stirring at the rotating speed of 600 rpm. Next, isoprene and acrylonitrile were mixed in a vessel cooled to 10° C. in a molar ratio of 1:1.3. N-nitrosodiphenylamine was added to the mixed solution such that the content thereof is 0.1% by weight to provide a raw material solution. The raw material solution was continuously supplied to the autoclave by a metering pump such that the residence time becomes 2 hours. During the reaction, the liquid level in the reactor was kept such that the volume of the gaseous phase over the reaction solution in the reactor is 30% relative to the entire volume of the reactor.

In addition, nitrogen gas was fed to the reactor to adjust the pressure in the autoclave to 45 kg/cm$^2$.G. Furthermore, the temperature of the liquid was kept at 185° C. for the continuous reaction.

As a result, methylcyanocyclohexene was continuously obtained with an average yield of 85% by mole based on isoprene used as the raw material. The pressure in the reactor was not changed or fluctuated suddenly in this example. Furthermore, the supplying amount of the raw material was not changed. The operation was stopped 15 days after initiation of the reaction to inspect in detail the inside of the reactor, the inlet pipe for the raw material and the outlet pipe for the reaction solution. No insoluble polymer was found to adhere to those surfaces.

Comparative Example 8

Example 14 was repeated to continuously prepare cyanocyclohexene except that the pipe for supplying the raw material was introduced directly into the liquid in the vessel type reactor, as shown in FIG. 4. In this comparative example, it became difficult to supply the raw material 1 day after initiation of the reaction, so the operation was stopped at that time and the inside of the pipe/reactor was inspected. It was found that a large amount of insoluble polymer had adhered to the inner surface of the supply pipe, especially at or around the surface of the outlet pipe for the raw material. The pipe was clogged.

Comparative Example 9

Example 15 was repeated except that the reactor as shown in FIG. 3 was used. The reactor was completely filled with the reaction solution to prepare methylcyanocyclohexene. However, this example suffered from a considerable fluctuation in pressure in the reactor and an increase in the inner temperature. The pressure fluctuated suddenly in the range of 35–55 kg/cm$^2$.G. There was a great possibility of damaging the reactor and auxiliary facilities. It was thus found difficult to prepare methylcyanocyclohexene continuously in a safe manner.

What is claimed is:

1. A process for preparing a Diels-Alder addition product by continuously reacting a conjugated diolefin and acrylonitrile while inhibiting production of insoluble polymers, said process comprising the steps of:
   providing a reactor which comprises a gaseous phase and a liquid phase;
   introducing an inert gas into the reactor to increase the pressure of the gaseous phase;
   releasing a premixed solution of the conjugated diolefin or a compound which produces the conjugated diolefin in the reactor and acrylonitrile through an upper portion of the reactor into the gaseous phase and dropping the premixed solution into the liquid phase;
   reacting the conjugated diolefin and acrylonitrile at a temperature of 180° C. to 200° C.; and
   removing a reaction product from a lower portion of the reactor.

2. The process as claimed in claim 1, wherein the volume of the gaseous phase is within the range of 10–50% relative to the entire volume of the reactor.

3. The process as claimed in claim 1, wherein the pressure during the reaction is within the range of 6–70 kg/cm$^2$.G.

4. The process as claimed in claim 1, wherein the inert gas is nitrogen, argon, helium, methane, ethane, propane, n-butane or isobutane.

5. The process as claimed in claim 1, wherein the compound from which the conjugated diolefin is produced is dicyclopentadiene, and the pressure during the reaction is within the range of 6–30 kg/cm$^2$.G.

6. The process as claimed in claim 5, wherein the pressure during the reaction is within the range of 6–10 kg/cm$^2$.G.

7. The process as claimed in claim 1 wherein the conjugated diolefin is butadiene and the pressure during the reaction is within the range of 50–70 kg/cm$^2$.G.

8. The process as claimed in claim 7, wherein the inert gas is nitrogen, argon, helium, methane or ethane.

9. The process as claimed in claim 1, wherein the conjugated diolefin is isoprene and the pressure during the reaction is within the range of 30–50 kg/cm$^2$.G.

10. The process as claimed in claim 9, wherein the inert gas is nitrogen, argon, helium, methane, ethane or propane.

11. The process as claimed in claim 1, wherein the premixed solution further comprises an N-nitrosoamine compound or a p-phenylenediamine compound.

12. The process as claimed in Claim 11, wherein the N-nitrosoamine compound is N-nitrosodimethylamine, N-nitrosodiethylamine, N-nitrosomethylethylamine, N-nitrosodiphenylamine, N-nitrosobenzylaniline or 4-nitroso-N,N-dimethylaniline.

13. The process as claimed in claim 11, wherein the p-phenylenediamine compound is N-phenyl-N'-isopropyl-p-phenylenediamine.

* * * * *